United States Patent
Reimerink-Schats et al.

(10) Patent No.: US 9,174,205 B2
(45) Date of Patent: Nov. 3, 2015

(54) PRODUCTION OF CATALYTICALLY ACTIVE ACTIVATED CARBONS

(75) Inventors: Wilhelmina Margaretha Theresia Maria Reimerink-Schats, Amersfoort (NL); Dirk van de Kleut, Hoogland (NL)

(73) Assignee: CABOT NORIT NEDERLAND B.V., Amersfoort (NL)

( * ) Notice: Subject to any disclaimer, the term of this patent is extended or adjusted under 35 U.S.C. 154(b) by 151 days.

(21) Appl. No.: 13/980,617

(22) PCT Filed: Jan. 25, 2012

(86) PCT No.: PCT/NL2012/050038
§ 371 (c)(1),
(2), (4) Date: Sep. 13, 2013

(87) PCT Pub. No.: WO2012/102610
PCT Pub. Date: Aug. 2, 2012

(65) Prior Publication Data
US 2014/0037536 A1    Feb. 6, 2014

(30) Foreign Application Priority Data
Jan. 25, 2011    (EP) .................................... 11151941

(51) Int. Cl.
| | |
|---|---|
| *C01B 31/10* | (2006.01) |
| *B01J 31/02* | (2006.01) |
| *C01B 31/08* | (2006.01) |
| *B01J 21/18* | (2006.01) |
| *B01J 35/00* | (2006.01) |
| *B01J 35/02* | (2006.01) |
| *B01J 35/10* | (2006.01) |
| *B01J 37/10* | (2006.01) |
| *C07F 9/38* | (2006.01) |
| *B01D 53/86* | (2006.01) |
| *C01B 13/02* | (2006.01) |

(52) U.S. Cl.
CPC ......... *B01J 31/0235* (2013.01); *B01D 53/8628* (2013.01); *B01J 21/18* (2013.01); *B01J 35/002* (2013.01); *B01J 35/023* (2013.01); *B01J 35/1023* (2013.01); *B01J 35/1028* (2013.01); *B01J 37/10* (2013.01); *C01B 13/0214* (2013.01); *C01B 31/082* (2013.01); *C01B 31/10* (2013.01); *C07F 9/3813* (2013.01); *B01D 2255/702* (2013.01)

(58) Field of Classification Search
CPC .............................. C01B 31/10; C01B 31/082
See application file for complete search history.

(56) References Cited

U.S. PATENT DOCUMENTS

| | | | |
|---|---|---|---|
| 3,953,345 | A | 4/1976 | Saito et al. |
| 4,118,341 | A | 10/1978 | Ishibashi et al. |
| 5,504,050 | A | 4/1996 | Hayden |
| 2009/0246110 | A1 | 10/2009 | Henning et al. |

FOREIGN PATENT DOCUMENTS

| | | |
|---|---|---|
| EP | 0 729 783 | 3/1996 |
| EP | 2 106 840 | 7/2009 |
| WO | WO 99/58240 | 11/1999 |
| WO | WO 01/05704 | 1/2001 |
| WO | WO 03/095368 | 11/2003 |

OTHER PUBLICATIONS

International Preliminary Report on Patentability for International Application No. PCT/NL2012/050038, mailed from WIPO on Aug. 8, 2013.
Barrett et al., The Determination of Pore Volume and Area Distributions in Porous Substances: I Computations from Nitrogen Isotherms, J. Am. Chem. Soc., 1951, 73, 373-380.
Cazorla-Amóros et al., $CO_2$ as Adsorptive to Characterize Langmuir 1998, 14, 4589-4596.
Juntgen, New Application for Carbonaceous Adsorbents, Carbon, 1977, 15, p. 273.
Marsh et al., Activated Carbon, 2006, Elsevier Ltd., p. 454-508.
Ritter et al., Pore-Size Distribution in Porous Materials: Pressure Porosimeter and Determination of Complete Macropore-Size Distributions, Ind. Eng. Chem. Analyt. Ed., 1945, 17, 782-786.
Sing et al., Reporting Physisorption Data for Gas/Solid Systems with Special Reference to the Determination of Surface Area and Porosity, Pure and Applied Chemistry, 1985, 57 (4), 603-619.
International Search Report for International Application No. PCT/NL2012/050038, mailed on Aug. 5, 2012.

*Primary Examiner* — Stuart Hendrickson

(57) ABSTRACT

The invention is directed to a method for preparing catalytically active activated carbon, to catalytically active activate carbon obtainable by the method, and to the use of the catalytically active activated carbon. The method of the invention method comprises the steps of: i) mixing charcoal with one or more organic nitrogen-containing compounds, said nitrogen-containing compounds comprising, next to a first nitrogen atom, at least two or more further heteroatoms selected from the group consisting of nitrogen and oxygen, wherein said further heteroatoms have a lone pair; ii) drying the mixture obtained in step i); iii) activating the dried mixture using steam, thereby producing catalytically active activated carbon.

12 Claims, 1 Drawing Sheet

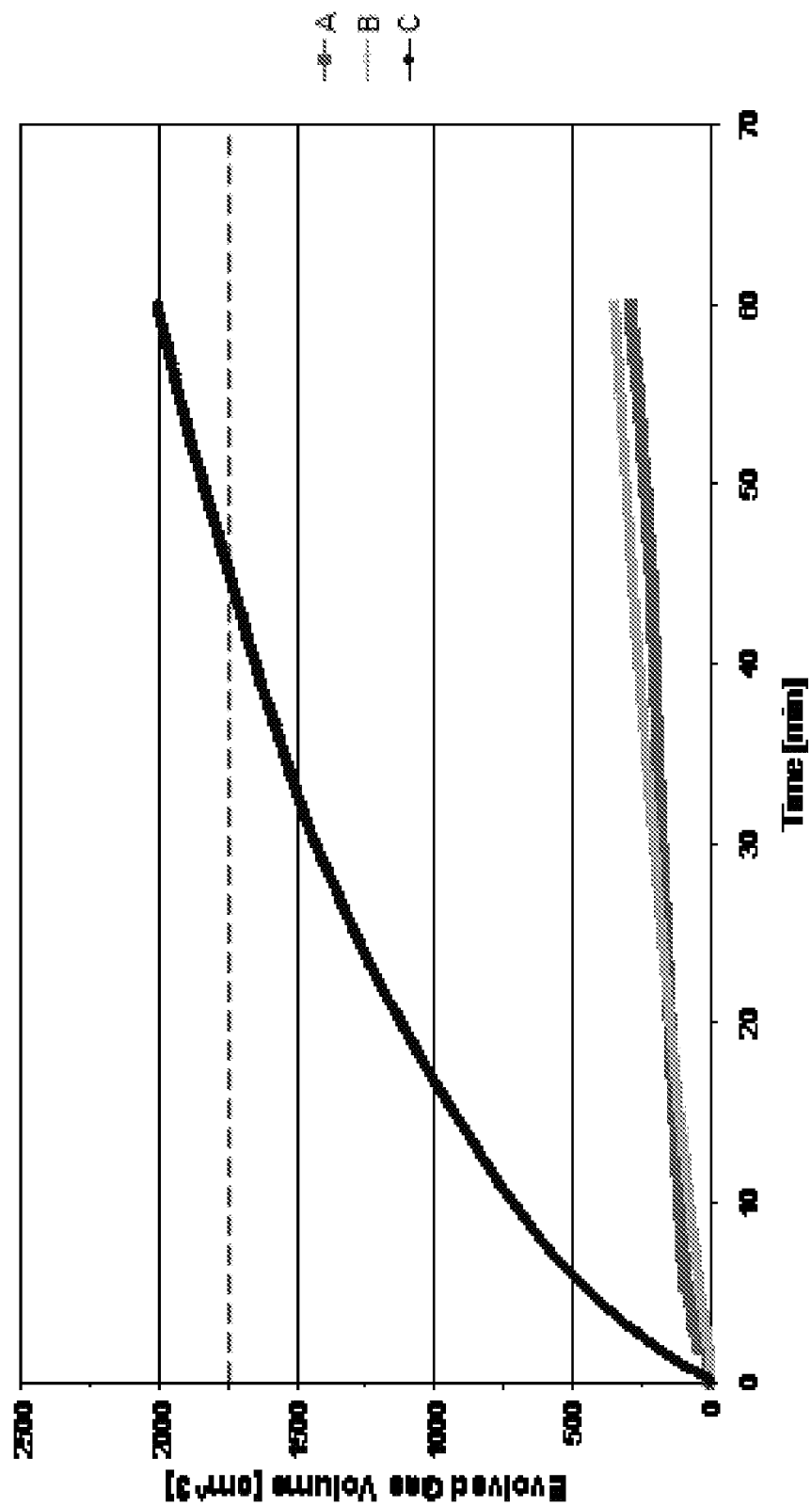

PRODUCTION OF CATALYTICALLY ACTIVE ACTIVATED CARBONS

CROSS-REFERENCE TO RELATED APPLICATIONS

This application is a national phase application under 35 U.S.C. §371 of International Application Number PCT/NL2012/050038, filed on Jan. 25, 2012, which claims priority to European Patent Application Number 11151941.9, filed on Jan. 25, 2011, the disclosure of which is incorporated herein by reference.

The invention is directed to a method for preparing catalytically active activated carbon, to catalytically active activated carbon obtainable by said method, and to the use of said catalytically active activated carbon.

Activated carbon is a carbonaceous adsorbent with a high internal porosity, and hence a large internal surface area. Commercial activated carbon grades typically have an internal surface area of 500-1500 $m^2/g$. Depending on the type of application, two major product groups of activated carbon exist:
i) powdered activated carbon (typically having a particle size of 1-200 μm, and
ii) granulated activated carbon (granulated or extruded) having a particle size in the 0.2-5 mm range.

A proper activated carbon has a number of unique characteristics, which i.a. include a large internal surface area, dedicated (surface) chemical properties and good accessibility of internal pores.

Micropores (having a diameter of less than 2 nm) generally contribute to the major part of the internal surface area. Macropores (having a diameter above 50 nm) and mesopores (having a diameter of 2-50 nm) can generally be regarded as the highways into the carbon particle, and are crucial for kinetics. The pore size distribution is highly important for the practical application; the best fit depends on the compounds of interest, the matrix (gas, liquid) and treatment conditions. The desired pore structure of an activated carbon product is attained by combining the right raw material and activation conditions.

Activated carbon is commonly used in a wide variety of different applications. Some examples of applications are decolourisation of sugar and sweeteners, drinking water treatment, gold recovery, production of pharmaceuticals and fine chemicals, catalytic processes, off gas treatment of waste incinerators, automotive vapour filters, colour/odour correction in wines and fruit juices, additive in liquorice, etc.

In its numerous applications, the activated carbon can perform one or more different functionalities including adsorption (through physical adsorption (Van der Waals forces) or chemisorption), reduction (e.g. removal of chlorine from water), catalysis (either as a catalyst or a carrier of a catalytic agent), carrier of biomass, carrier of chemicals (e.g. slow release applications) and colourant.

For the activated carbon to be used as a catalyst it is of course required that the activated carbon has catalytic activity. In the art, several processes have been described for preparing catalytically active activated carbon.

For example, WO-A-99/58240 describes a process for the production of carbonaceous chars having catalytic activity. The method includes combining relatively small amounts of a nitrogen-containing compound with a nitrogen-poor carbonaceous feedstock, carbonising the mixture at temperatures less than 600° C. in an oxidising environment, and then activating the resultant carbonised/oxidised product at temperatures greater than 600° C. A disadvantage of the method disclosed in this patent publication is that it requires the carbonaceous feedstock to be subjected to a carbonising/oxidising step prior to the activation step. Furthermore, this patent publication only discloses unsustainable sources of carbonaceous feedstock, such as bituminous coal, subbituminous coal, lignite coal and anthracite coal.

In view of the undesirable contribution of these unsustainable sources of carbonaceous feedstock to the concentration of greenhouse gases in the atmosphere, there is a strong demand for a process for preparing catalytically active activated carbon in which a sustainable source of carbonaceous feedstock is used.

Although a production process for catalytically active activated carbon using wood char as a sustainable source of carbonaceous feedstock is known from WO-A-03/095368, this process involves addition of ammonia to steam. Such addition of ammonia is highly undesirable both from a health perspective, as well as from an environmental perspective, which makes it very difficult to practice the process described in this patent publication safely on an industrial scale.

An objective of the invention is to at least partly meet the aforementioned demand for a preparation process of catalytically active activated carbon in which a sustainable source of carbonaceous feedstock is used. A further objective of the invention is to provide a safe alternative to a process wherein ammonia is added to steam. Yet a further objective of the invention is to provide a method for producing catalytically active activated carbon starting from a carbonaceous feedstock, wherein the carbonaceous feedstock does not have to be subjected to a carbonising/oxidising step in said method.

Accordingly, in a first aspect, the invention is directed to a method for preparing catalytically active activated carbon comprising micropores, mesopores and macropores, said method comprising the steps of:
i) mixing charcoal with one or more organic nitrogen-containing compounds, said nitrogen-containing compounds comprising, next to a first nitrogen atom, at least two or more further heteroatoms selected from the group consisting of nitrogen and oxygen, wherein said further heteroatoms have a lone pair;
ii) drying the mixture obtained in step i);
iii) activating the dried mixture using steam, thereby producing catalytically active activated carbon.

The process of the invention advantageously allows the preparation of a catalytically active activated carbon in a minimum of process steps starting from charcoal as a sustainable carbonaceous feedstock. It is highly advantageous that the process of the invention does not require the conventional carbonising/oxidising step. Thereby, the presently claimed method does not only have less process steps, but in addition allows saving investment costs relating to additional equipment that is required for carrying out this carbonising/oxidising conversion.

The term "charcoal" as used in this application is meant to refer to the black residue consisting of impure carbon obtained by removing water and other volatile constituents from animal and vegetation substances. Charcoal is usually produced by slow pyrolysis, the heating of wood, sugar, bone char, or other substances in the absence of oxygen (see pyrolysis, char and biochar). In contrast to fossil coals (such as pit coal, bituminous coal, subbituminous coal, brown coal, lignite coal, and anthracite coal), charcoal is sustainable. In an embodiment, the charcoal applied in the invention is wood char. The term wood char is meant to refer to the hard fibrous product that is formed when wood is at least partially pyrolised and/or thermochemically treated, or otherwise converted to carbon to some extent.

The term "activated carbon" as used in this application is meant to refer to carbon materials having a predominantly amorphous character with a large surface area and a considerable porosity.

The term "catalytically active" as used in this application in reference to a carbon is defined as having a hydrogen peroxide decomposition parameter $t_{1/4}$ of 60 minutes or less using the hydrogen peroxide conversion test as described in the Examples. The term "catalytically inactive" as used in this application in reference to carbon is defined as having a $t_{1/4}$ of more than 60 minutes using the hydrogen peroxide decomposition test as described in the Examples.

The charcoal may be in the form of charcoal chunks, charcoal chips, charcoal powder, and/or any other form. From a practical point of view, it is preferred that the charcoal that is to be mixed with the one or more nitrogen-containing compounds is present in the form of pieces having a particle size of 10 cm or less, preferably 10 mm or less, such as in the range of 5 mm to 10 µm.

The catalytically active activated carbon that is obtained by the method of the invention comprises micropores, mesopores and macropores. It is well known to the person skilled in the art that micropores are defined by a pore diameter of less than 2 nm, mesopores are defined by a pore diameter in the range of 2-50 nm, while macropores are defined by a pore diameter of more than 50 nm (such as in the range of 50-1000 nm), see for instance *Pure and Applied Chemistry* 1985, 57(4), 603-619. The pore size distribution of the catalytically active activated carbon can, for example, be determined by nitrogen adsorption isotherm (for micropores and mesopores, see Barrett et al., *J. Am. Chem. Soc.* 1951, 73, 373-380) and mercury porosimetry (for macropores, see Ritter et al., *Ind. Eng. Chem. Analyt. Ed.* 1945, 17, 782-786).

Hence, the invention is clearly distinguished from carbon molecular sieves, such as described in EP-A-0 729 783, which have a highly uniform and highly narrow pore size distribution (Cazorla-Amorós et al., *Langmuir* 1998, 14, 4589-4596). In this way carbon molecular sieves have a pore size distribution which is clearly distinguished from the catalytically active activated carbon that is prepared by the method of the present invention. The difference between carbon molecular sieves and activated carbon has, for instance, been discussed by Jüntgen (Carbon 1977, 15, 273).

In an embodiment, the mixture obtained in after mixing the charcoal with the one or more nitrogen-containing compounds is catalytically inactive.

It is preferred that the one or more nitrogen-containing compounds comprise one or more moieties selected from the group consisting of amines, amides, nitrils, nitrosamines, cyanates, isocyanates, and oximes. More preferably, the one or more nitrogen-containing compounds comprise two or more groups selected from the group consisting of —NH$_2$, =O, —OH, and =NH or —NH—.

The nitrogen-containing compounds can for instance be selected from the group consisting of one or more nitrogen-containing compounds selected from the group consisting of urea, N-butylurea, biuret, 2-cyanoguanidine, guanidine, biguanide, cyanuric acid, creatinine, ammeline, ammelide, hexamethylenetetramine, melamine, ammonium lignosulphonate, and derivatives thereof. A preferred nitrogen-containing compound is urea.

The amount of the nitrogen-containing compound(s) in the mixture can be selected such that the amount of nitrogen atoms is in the range of 0.1-8 wt. % based on the total weight of the charcoal, such as in the range of 1-7 wt. %, or 2-5 wt. %. If the applied amount of nitrogen-containing compound(s) is less than an amount corresponding to 0.1 wt. % of nitrogen atoms based on the total weight of the charcoal, then insufficient catalytic activity will achieved. On the other hand, very high amounts of nitrogen-containing compound(s) will lead to undesirable high costs.

Mixing of the charcoal and the nitrogen-containing compound can be performed by impregnation, stirring, or the like. Such mixing methods are well-known to the person skilled in the art. The mixing may involve dissolving of solid nitrogen-containing compounds in a suitable solvent (such as water) prior to impregnation of charcoal. Mixing can suitably be performed at a temperature between ambient and about 100° C. The mixing time can vary widely and may range from 1 second to 10 hours.

After mixing the charcoal with the one or more nitrogen-containing compounds, the obtained mixture is dried. Drying may be carried out in a conventional oven, a belt dryer, fluidised bed dryer, rotary dryer or the like. Drying is typically performed at temperatures in the range of 70-200° C. The mixture can be dried for a time of 10 minutes to 10 hours.

During the drying step, the moisture content of the mixture is preferably reduced to a value of 10 wt. % or less based on total weight of the mixture, preferably a value of 5 wt. % or less, such as in the range of 5-0.01 wt. %.

In a further step, the dried mixture of charcoal and one or more nitrogen-containing compounds is subjected to steam activation. During steam activation the dried mixture is activated, i.e. a higher internal surface area and pore volume is created, and the mixture becomes catalytically active at the same time. In absence of steam, the mixture does not show catalytic activity after a heat treatment. This is in contrast to the properties of the carbonaceous materials described in WO-A-99/58240, which form an activatable char that is already catalytically active after the carbonising step and before activation. Therefore, in accordance with an embodiment of the invention the dried mixture entering the steam activation in step iii) of the method of the invention is catalytically inactive.

In an embodiment of the invention, the mixture of charcoal with the one or more organic nitrogen-containing compounds is not carbonised before being subjected to steam activation. Carbonisation in this respect is defined as a process by which solid residues with increasing content of the element carbon are formed from organic material usually by pyrolysis in an inert atmosphere (Marsh et al., *Activated Carbon*, 2006, Elsevier Ltd.). Typically, carbonisation involves a temperature of 400° C. or more.

Steam activation of carbon is a well-known process step. On a small scale, steam activation can be realised by introducing steam into an oven with the heated mixture of charcoal and nitrogen-containing compound(s). On a larger scale, e.g. in a commercial continuous process, the mixture of charcoal and nitrogen-containing compound(s) can be introduced separate from steam into a furnace or kiln operating at the desired activation temperature. Typically, the mixture of charcoal and nitrogen-containing compound(s) is activated at a temperature in the range of 600-1200° C., preferably a temperature in the range of 700-1100° C.

During the steam activation process carbon from the charcoal is partly gasified with steam. Due to this gasification process, new micropores are created and existing pores are widened, resulting in a higher pore volume and a higher surface area. The extent of activation of an activated carbon can be expressed with the burn-off, defined as the weight percentage of material lost due to the carbon gasification process. The burn-off is determined by measuring the carbon yields when charcoal is submitted to heat treatments in inert gas and in steam activation gases. The burn-off is calculated by dividing the difference in yields of the heat treatment in inert gas and in steam activation gases, with the yield in inert gas. The steam activation step preferably results in a burn-off in the range of 10-80 wt. %, preferably in the range of 20-60 wt. %.

During the steam activation pores are created in the carbon. The steam activation period and the steam dosing rate allow control over the pore size distribution that is obtained and thereby tuning the internal surface area of the catalytically active activated carbon obtained.

After steam activation, a carbon is obtained that is both activated (made porous), as well as catalytically active.

Contacting the hot catalytically active activated carbon with air could lead to undesired oxidation of the carbon. Therefore, the catalytically active activated carbon is preferably cooled in the reaction gases of the steam activation step. The activated carbon can, for instance, be cooled to a temperature of 250° C. or less.

Depending on the intended application the catalytically active activated carbon may be provided in powder form or in granules.

If it is desired to obtain a catalytically active activated carbon in powder form, then the activated carbon can be milled accordingly to the desired particle size range.

If the intended application, on the other hand, demands a catalytically active activated carbon in granular form, then granules can be prepared by breaking and sieving the catalytically active activated carbon to the right particle size range. Alternatively, mixtures of fine charcoal particles and nitrogen-containing compound(s) can be shaped prior to activation by the inclusion of one or more binders. After activation, the resulting shaped catalytically active activated carbon particles may be used as such in the application, or they may be crushed and/or sieved in a more suitable particle size range. Such shaping procedures using binders allows the preparation of shaped particles which may be advantageous, e.g. in gas phase applications. Suitable binder materials include molasses, starch, chitosan, alginate, cellulose acetate, formaldehydes, ammonium lignosulphonate, as well as inorganic binder materials such as bentonite. The binder can, for instance, be introduced during the step of mixing the charcoal with the nitrogen-containing compound. A preferred binder is ammonium lignosulphonate, because it can serve at the same time as a binder and as a nitrogen-containing compound.

The nitrogen-containing compounds can have a molecular weight of 525 g/mol or less. Binder nitrogen-containing compounds can, for example, have a molecular weight in the range of 250-525 g/mol, such as in the range of 300-525 g/mol. Non-binder nitrogen-containing compounds can, for example, have a molecular weight of 150 g/mol or less, such as 130 g/mol or less or in the range of 50-130 g/mol.

The catalytically active activated carbon obtainable by the method of the invention has unique properties, not only because of the charcoal starting material, but also due to the meticulously chosen combination of process steps.

Therefore, in a further aspect the invention is directed to a catalytically active activated carbon obtainable by the method of the invention.

The catalytically active activated carbon of the invention preferably has a catalytic activity (expressed as a hydrogen peroxide conversion parameter $t_{1/4}$ using the hydrogen peroxide decomposition test as described in the Examples) of 60 minutes or less, preferably 45 minutes or less, such as in the range of 1-30 minutes.

The catalytically active activated carbon obtainable by the method of the invention typically has a packed density (for granules: apparent density (ASTM D2854-89) and for powders: tamped density (DIN ISO 787.11)) of 550 g/l or less, such as in the range of 200-550 g/l. This is in contrast to catalytically active coal obtained from fossil starting materials, which has a higher packed density such as in the range of 550-800 g/l.

Advantageously, the catalytically active activated carbon of the invention has a high internal surface area. The internal surface area is preferably 500 $m^2/g$ or more, as determined by a nitrogen isotherm combined with a BET calculation method according to ASTM D 3663. More preferably, the internal surface area is in the range of 750-2000 $m^2/g$, such as in the range of 900-2000 $m^2/g$, most preferably in the range of 905-1500 $m^2/g$.

A measure for the micropore volume of activated carbons can be established by measuring the Iodine Number according to ASTM D4607-94. A higher value for the Iodine Number corresponds to a higher micropore volume. The iodine number of the catalytically active activated carbon of the invention is preferably in the range of 400-2000 mg/g as determined by ASTM D4607-94, more preferably in the range of 400-1500 mg/g, even more preferably in the range of 800-1500 mg/g.

If the catalytically active activated carbon of the invention is in powder form, then the activated carbon particles can have an average particle size in the range of 1-150 µm, preferably in the range of 2-100 µm. The average particle sizes can be determined by laser diffraction analysis.

On the other hand if the catalytically active activated carbon is used in the form of granules, then the granules can have an average particle size in the range of 0.2-5 mm, preferably in the range of 0.5-4 mm, and more preferably in the range of 0.8-3 mm. The granules may have any suitable shape, such as disks, spheres, cubes, pellets, briquettes etc.

The catalytically active activated carbon of the invention can be used in a wide variety of catalytic applications. For example, the catalytically active activated carbon can act as a catalyst for gas phase application (e.g. $NO_x$ removal and $SO_x$ oxidation), and for liquid phase applications (e.g. peroxide destruction, chloramine removal, and glyphosate production). Accordingly, in yet a further aspect the invention is directed to the use of the catalytically active activated carbon of the invention as a catalyst in gas phase or liquid phase applications.

The invention will now be further illustrated by means of the following non-limitative Examples. In the examples, urea is used as the nitrogen-containing compound. Urea serves as a representative example for the range of nitrogen-containing compounds defined in claim 1.

EXAMPLES

A sample of wood char was broken and sieved to obtain particles in the sieve range 2-30 mm. The sized material was split in three equal portions.

A first portion was first dried at 120° C. for 180 minutes. The dried sample was activated with steam by introducing the dried product in a rotary kiln kept at 1050° C. in a gas flow containing steam and nitrogen. After 5 hours the activated carbon was removed from the rotary kiln and cooled down to near room temperature in the same gas flow. The resulting comparative sample was labeled 'A'.

The second and third portions were impregnated with an aqueous urea solution containing 67 g urea/l by submerging the wood char particles in the solution for several hours. Subsequently, the impregnated wood char was separated from the solution and dried at 120° C. for 180 minutes. Both portions impregnated dried product were heat treated in a rotary kiln kept at 1050° C. A first impregnated dried portion was heat treated in the kiln in a gas flow containing steam and nitrogen for 5 hours, whereas the second impregnated dried portion was heat treated in a gas flow containing only nitrogen for 5 hours. The heat treated samples were removed from the rotary kiln and cooled down to near room temperature without changing the composition of the gas flow. The impregnated dried sample submitted to heat treatment in nitrogen was labeled comparative sample 'B', and the impregnated dried sample submitted to steam activation conditions was labeled inventive sample 'C'.

The Iodine Number of comparative samples 'A' and 'B', and inventive sample 'C' were 655 mg/l, 30 mg/l and 935 mg/l, respectively, as determined according to ASTM D4607-94. The nitrogen iso BET surface area of the samples 'A', 'B', and 'C' were 905 m$^2$/g, 94 m$^2$/g and 995 m$^2$/g, respectively, as determined according to ASTM D 3663. Based on the method developed by Barrett (*J. Am. Chem. Soc.* 1951, 73, 373-380) several parameters related to micropores (pores less than 1 nm in radius) and mesopores (pores between 1 and 25 nm in radius) are calculated. The macropore volume has been determined according to the mercury porosimetry method developed by Ritter et al. (*Ind. Eng. Chem. Analyt. Ed.* 1945, 17, 782-786).

|  | Sample A | Sample B | Sample C |
| --- | --- | --- | --- |
| Micropore volume (cm$^3$/g) [1] | 0.377 | 0.0394 | 0.415 |
| Mesopore volume (cm$^3$/g) [1] | 0.0720 | 0.00957 | 0.0805 |
| Macropore volume (cm$^3$/g) | 1.08 | 0.667 | 1.03 |
| Average micropore radius (V/A) (nm) [2] | 0.345 | 0.327 | 0.353 |
| Average pore radius (2 V/A) (nm) [1] | 3.17 | 3.68 | 3.24 |

[1] According to the so-called BJH-method described by Barrett et al. (*J. Am. Chem. Soc.* 1951, 73, 373-380)
[2] According to the so-called MP-method described by Mikhail et al. (*J. Colloid Interface Sci.* 1968, 26, 45-53)

The ash content of the carbon samples was determined according to ASTM D 2866 (sample 'A' 2.54%, sample 'B' 2.61%, and sample 'C' 2.54%). The measurement of the apparent density (ASTM D 2854-89) for sample 'A', 'B', and 'C' gave values of 222 g/l, 310 g/l, and 246 g/l, respectively. The established burn-off after the activation procedure of samples 'A', 'B', and 'C' were found to be 53%, 0% and 37%, respectively.

Samples of the obtained products were milled and tested on catalytic activity in the hydrogen peroxide decomposition test described below.

The total gas volumes evolved during the hydrogen peroxide decomposition test have been presented in FIG. 1 for all samples, wherein the dashed horizontal line indicates at which volume the $t_{1/4}$ is read out. The catalytic activity is expressed as $t_{1/4}$ in minutes, i.e. the time required to convert 25% of the hydrogen peroxide into oxygen gas in an aqueous solution under defined isothermal conditions.

The catalytic activity parameter $t_{1/4}$ of inventive sample 'C' was found to be 45 minutes. Comparative samples 'A' and 'B' showed no catalytic activity, i.e. the values for $t_{1/4}$ were more then 60 minutes. These values show that only catalytic activity was measured for the sample subjected to the procedure according this invention.

Hydrogen Peroxide Decomposition Test

The catalytic activity of activated carbon can be determined by measuring the decomposition rate of hydrogen peroxide under controlled conditions. For this, a fixed amount of powdered activated carbon (150 mg) is dispersed in a mixture of 100 ml demineralised water and 50 ml aqueous potassium phosphate buffer solution (containing 68 g/l $KH_2PO_4$ and 87 g/l K2HPO4), contained in a thermostatically controlled and magnetically stirred vessel at 60° C. At time t=0 minutes, 50 ml of a solution containing 35 wt. % of hydrogen peroxide is added to the vessel and the amount of gas evolved is registered as a function of time. The hydrogen peroxide conversion rate parameter $t_{1/4}$ is defined as the time in minutes until a total gas volume of 1.75 liter has been generated in the reaction vessel. The parameter $t_{1/4}$ is used as a measure for the catalytic activity of powdered activated carbon. In order to establish $t_{1/4}$ for granular activated carbons, granular carbons are milled to powder before the test.

The invention claimed is:

1. Method for preparing catalytically active activated carbon comprising micropores, mesopores and macropores, said method comprising the steps of:
   i) mixing charcoal with one or more organic nitrogen-containing compounds, said nitrogen-containing compounds comprising one or more moieties selected from the group consisting of amines, amides, nitriles, nitrosamines, cyanates, isocyanates, and oximes;
   ii) drying the mixture obtained in step i);
   iii) activating the dried mixture using steam, thereby producing catalytically active activated carbon,
   wherein the mixture obtained in step i) is not carbonised before being activated using steam in step iii).

2. Method according to claim 1, wherein the one or more nitrogen-containing compounds comprise two or more groups selected from the group consisting of —$NH_2$, =O, —OH, =NH and —NH—.

3. Method according to claim 1, wherein the one or more nitrogen-containing compounds are selected from the group consisting of urea, N-butylurea, biuret, 2-cyanoguanidine, guanidine, biguanide, cyanuric acid, creatinine, ammeline, ammelide, hexamethylenetetramine, melamine, ammonium lignosulphonate, and derivatives thereof.

4. Method according to claim 1, wherein said charcoal is wood char.

5. Method according to claim 1, wherein said charcoal is in the form of charcoal chunks, charcoal chips, and/or charcoal powder.

6. Method according to claim 1, wherein the dried mixture entering the steam activation in step iii) is catalytically inactive.

7. Method according to claim 1, wherein in step ii) the mixture is dried to a moisture content of 10 wt. % or less based on total weight.

8. Method according to claim 1, wherein the steam activation of step iii) results in a burn-off of 10-80 wt. %.

9. Method according to claim 1, wherein the amount of the one or more nitrogen-containing compounds in the mixture is such that the amount of nitrogen atoms is 0.1-8 wt. % based on the total weight of the charcoal.

10. Method according to claim 1, wherein said catalytically active activated carbon is in particulate form having particles with an average particle size of 1-200 μm as determined by laser diffraction, or in granulate form having granules with an average particle size of 0.2-5 mm.

11. Method according to claim 10, wherein said catalytically active activate carbon has a hydrogen peroxide conversion time using the hydrogen peroxide conversion test as described herein of 40 minutes or less.

12. Method according to claim 10, wherein said catalytically active activate carbon has an iodine number in the range of 400-2000 mg/g as determined by ASTM D4607-94.

* * * * *